(12) United States Patent
Amidon et al.

(10) Patent No.: US 8,399,016 B2
(45) Date of Patent: Mar. 19, 2013

(54) SUSTAINED-RELEASE TABLET COMPOSITION OF PRAMIPEXOLE

(75) Inventors: Gregory Everett Amidon, Portage, MI (US); Loksidh Devi Ganorkar, Kalamazoo, MI (US); John Mark Heimlich, Portage, MI (US); Ernest J. Lee, Kalamazoo, MI (US); Robert Martin Noack, Ann Arbor, MI (US); Joseph Peter Reo, Kalamazoo, MI (US); Connie Jo Skoug, Portage, MI (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 108 days.

(21) Appl. No.: 12/716,755

(22) Filed: Mar. 3, 2010

(65) Prior Publication Data

US 2010/0316710 A1    Dec. 16, 2010

Related U.S. Application Data

(63) Continuation of application No. 10/626,166, filed on Jul. 23, 2003, now abandoned.

(60) Provisional application No. 60/479,513, filed on Jun. 18, 2003, provisional application No. 60/398,447, filed on Jul. 25, 2002, provisional application No. 60/398,427, filed on Jul. 25, 2002.

(51) Int. Cl.
*A61K 9/22* (2006.01)

(52) U.S. Cl. ........ 424/468; 424/464; 424/474; 424/475; 424/480; 424/482

(58) Field of Classification Search .................. None
See application file for complete search history.

(56) References Cited

U.S. PATENT DOCUMENTS

| | | | |
|---|---|---|---|
| 2,887,440 A | 5/1959 | Greminger, Jr. et al. |
| 3,845,770 A | 11/1974 | Theeuwes et al. |
| 4,036,948 A | 7/1977 | Kitamori et al. |
| 4,140,755 A | 2/1979 | Sheth et al. |
| 4,424,235 A | 1/1984 | Sheth et al. |
| 4,656,027 A | 4/1987 | Sjöqvist |
| 4,709,712 A | 12/1987 | Bordovsky et al. |
| 4,731,374 A | 3/1988 | Griss et al. |
| 4,738,851 A | 4/1988 | Schoenwald et al. |
| 4,886,812 A | 12/1989 | Griss et al. |
| 5,026,559 A | 6/1991 | Eichel et al. |
| 5,078,991 A | 1/1992 | Birtwistle et al. |
| 5,133,974 A | 7/1992 | Paradissis et al. |
| 5,273,975 A | 12/1993 | Moon et al. |
| 5,431,920 A | 7/1995 | Bechard |
| 5,458,887 A | 10/1995 | Chen et al. |
| 5,472,712 A | 12/1995 | Oshlack et al. |
| 5,656,296 A | 8/1997 | Khan et al. |
| 6,056,977 A | 5/2000 | Bhagwat et al. |
| 6,126,959 A | 10/2000 | Levine et al. |
| 6,197,339 B1 | 3/2001 | Ju |
| 6,221,396 B1 | 4/2001 | Chao et al. |
| 6,248,358 B1 | 6/2001 | Bologna et al. |
| 6,277,875 B1 | 8/2001 | Holman |
| 6,340,475 B2 | 1/2002 | Shell et al. |
| 6,451,343 B1 | 9/2002 | Glinecke et al. |
| 6,467,637 B2 | 10/2002 | Riga |
| 6,558,701 B2 | 5/2003 | Bartholomaeus et al. |
| 6,624,200 B2 | 9/2003 | Bologna et al. |
| 6,667,060 B1 | 12/2003 | Vandecruys et al. |
| 6,727,367 B2 | 4/2004 | Pospisilik |
| 7,153,845 B2 | 12/2006 | Levine et al. |
| 2002/0010216 A1 | 1/2002 | Rogosky et al. |
| 2002/0015735 A1 | 2/2002 | Hedden et al. |
| 2002/0103240 A1 | 8/2002 | Pospisilik |
| 2002/0114831 A1 | 8/2002 | Norden et al. |
| 2002/0132850 A1 | 9/2002 | Bartholomaeus et al. |
| 2003/0077297 A1 | 4/2003 | Chen et al. |
| 2003/0133982 A1 | 7/2003 | Heimlich et al. |
| 2003/0180352 A1 | 9/2003 | Patel et al. |
| 2004/0068119 A1 | 4/2004 | Pospisilik |
| 2004/0122104 A1 | 6/2004 | Hirsh et al. |
| 2005/0020589 A1 | 1/2005 | Ganorkar et al. |
| 2005/0175691 A1 | 8/2005 | Lee et al. |
| 2005/0226926 A1 | 10/2005 | Amidon et al. |
| 2006/0051417 A1 | 3/2006 | Friedl et al. |
| 2006/0051419 A1 | 3/2006 | Friedl et al. |
| 2006/0198887 A1 | 9/2006 | Friedl et al. |
| 2007/0196481 A1 | 8/2007 | Amidon et al. |
| 2008/0031945 A1 | 2/2008 | Eisenreich et al. |
| 2009/0041844 A1 | 2/2009 | Friedl et al. |
| 2009/0098202 A1 | 4/2009 | Friedl et al. |
| 2009/0130197 A1 | 5/2009 | Friedl et al. |
| 2009/0143387 A1 | 6/2009 | Amidon et al. |

FOREIGN PATENT DOCUMENTS

| | | |
|---|---|---|
| CA | 1263653 | 12/1989 |
| CA | 2455585 A1 | 2/2003 |
| DE | 19906290 | 8/2000 |
| EP | 0186087 | 7/1986 |
| EP | 0895780 A1 | 2/1999 |
| EP | 0933079 A1 | 8/1999 |
| GB | 2097676 | 11/1982 |
| GB | 2338186 | 12/1999 |
| WO | 9015058 A1 | 12/1990 |
| WO | 9201443 A1 | 2/1992 |
| WO | 9704752 A1 | 2/1997 |
| WO | 9855107 A1 | 12/1998 |

(Continued)

OTHER PUBLICATIONS

Biglan et al.; A review of pramipexole and its clinical utility in Parkinson's disease; Expert Opinion on Pharmacotherapy; 2002; vol. 3; No. 2; pp. 197-210.
British National Formulary; 41$^{st}$ ed.; 2001; 196.
Colosimo et al.; Motor fluctuations in Parkinson's disease: pathophysiology and treatment; European Journal of Neurology; 1999; vol. 6; No. 1; pp. 1-21.
Dooley et al.; Pramipexole: A Review of its Use in the Management of Early and Advanced Parkinson's Disease; Drugs & Aging; 1998; vol. 12; No. 6; pp. 495-514.

(Continued)

*Primary Examiner* — James Rogers
(74) *Attorney, Agent, or Firm* — Michael P. Morris; Philip I. Datlow

(57) ABSTRACT

A sustained-release pharmaceutical composition in a form of an orally deliverable tablet comprises a water-soluble salt of pramipexole, dispersed in a matrix comprising a hydrophilic polymer and a starch having a tensile strength of at least about 0.15 kN cm$^{-2}$ at a solid fraction representative of the tablet.

6 Claims, 4 Drawing Sheets

FOREIGN PATENT DOCUMENTS

| | | | |
|---|---|---|---|
| WO | 9901121 | A1 | 1/1999 |
| WO | 9909066 | A1 | 2/1999 |
| WO | 9916442 | A2 | 4/1999 |
| WO | 9945924 | A1 | 9/1999 |
| WO | 0010536 | A1 | 3/2000 |
| WO | 0059477 | A1 | 10/2000 |
| WO | 0101973 | A2 | 1/2001 |
| WO | 0110405 | A1 | 2/2001 |
| WO | 0119337 | A2 | 3/2001 |
| WO | 0122820 | A1 | 4/2001 |
| WO | 03013521 | A1 | 2/2003 |
| WO | 03053402 | A1 | 7/2003 |
| WO | 2004010982 | A1 | 2/2004 |
| WO | 2004010997 | A1 | 2/2004 |
| WO | 2004010998 | A1 | 2/2004 |
| WO | 2004010999 | A1 | 2/2004 |
| WO | 2004080440 | A1 | 9/2004 |
| WO | 2004087175 | A1 | 10/2004 |
| WO | 2006015942 | A1 | 2/2006 |
| WO | 2006015943 | A2 | 2/2006 |
| WO | 2006015944 | A2 | 2/2006 |
| WO | 2006046256 | A1 | 5/2006 |
| WO | 2007002516 | A2 | 1/2007 |
| WO | 2007002518 | A1 | 1/2007 |
| WO | 2007022182 | A1 | 2/2007 |
| WO | 2007054976 | A2 | 5/2007 |
| WO | 2007090881 | A2 | 8/2007 |
| WO | 2007090882 | A2 | 8/2007 |
| WO | 2007090883 | A1 | 8/2007 |
| WO | 2008015162 | A1 | 2/2008 |

OTHER PUBLICATIONS

Elkheshen et al.; In vitro and in vivo Evaluation of Floating Controlled Release Dosage Forms of Verapamil Hydrochloride; Pharm. Ind.; 2004; vol. 66; No. 11; pp. 1364-1372.

Elkheshen et al.; Per-oral Extended-Release Bioadhesive Tablet Formulation of Verapamil HCl; Bollettino Chimico Farmaceutico, Societa Editoriale Farmaceutica, Milano, 2002; vol. 142; No. 5; pp. 226-231.

Forbes et al.; Progress in Neurology and Psychiatry; vol. 7; No. 2; pp. 10-14, 2003.

Hiestand et al.; Indices of Tableting Performance; Powder Technology; 1984; vol. 38; pp. 145-159.

Hiestand et al.; Tablet bond. II. Experimental check of model; International Journal of Pharmaceutics; 1991; vol. 67; pp. 231-246.

Hubble et al.; Pramipexole in Patients with Early Parkinson's Disease; Clinical Neuropharmacology; vol. 18; No. 4; pp. 338-347, 2003.

Hubble; Pre-clinical studies of pramipexole: clinical relevance; European Journal of Neurology Suppl.; May 2000; vol. 7; No. Supplement 1; pp. 15-20.

Lemke; Effect of Reboxetine on Depression in Parkinson's Disease in Patients; Journal of Clinical Psychiatry; 2002; vol. 63; No. 4; pp. 300-304.

Mierau et al.; Pramipexole binding and activation of cloned and expressed dopamine D2, D3 and D4 receptors; European Journal of Pharmacology Molecular Pharmacology Section 290; 1995; pp. 29-36.

Mierau; Pramipexole: A Dopamine-Receptor Agonist for Treatment of Parkinson's Disease; Clinical Neuropharmacology; vol. 18; Supp 1; 1995 Raven Press; pp. S195-S206.

Nur et al.; Captopril Floating and/or Bioadhesive Tablets: Design and Release Kinetics; Drug Development and Industrial Pharmacy; 2000; vol. 26; No. 9; pp. 965-969.

Physicians' Desk Reference; 37th Edition; 2003; pp. 2768-2772.

Remington Farmacia 1988; Alfonso R. Gennaro; 19a Edition; Panamericana Espana; pp. 2470.

Santus; An in vitro-in viro investigation of oral bioadhesive controlled release furosemide formulations; European Journal of Pharmaceutics and Biopharmaceutics; 1997; vol. 44; pp. 39-52.

Scheife et al.; Impact of Parkinson's disease and its pharmacologic treatment on quality of lie and economic outcomes; American Journal of Health System Pharmacy; May 15, 2000; vol. 57; No. 10; pp. 953-962.

The Merck Index; Thirteenth Edition; Merck & Co., Inc., Whitehouse Station, NJ, USA, 2001.

Tonson et al.; Compaction Properties of Pregelatinized Starch (Starch 1500 TM): Self-Lubrication; abstract taken from AIChE 2006 Spring National Meeting Preliminary Program; found at: http://aiche.confex.com/aiche/s06/preliminaryprogram/abstract-33412.htm.

USP 24th Edition; 2000; pp. 1941-1943.

Wright et al.; Steady-State Pharmacokinetic Properties of Pramipexole in Healthy Volunteers; Journal of Clinical Pharmacology; 1997; vol. 37; pp. 520-525.

Non-final Office Action dated Aug. 5, 2009 from U.S. Appl. No. 11/202,713, filed Aug. 12, 2005; Friedl et al.

SUSTAINED-RELEASE TABLET COMPOSITION OF PRAMIPEXOLE

This application claims priority of U.S. provisional application Ser. No. 60/398,427 filed on Jul. 25, 2002; U.S. provisional application Ser. No. 60/398,447 filed on Jul. 25, 2002; and U.S. provisional application Ser. No. 60/479,513 filed on Jun. 18, 2003.

FIELD OF THE INVENTION

The present invention relates to tablet formulations, and more particularly to a sustained-release tablet composition for oral delivery of a water-soluble drug or prodrug, exemplified by pramipexole dihydrochloride.

BACKGROUND OF THE INVENTION

Many active pharmaceutical agents, including drugs and prodrugs, have been formulated as orally deliverable dosage forms providing sustained release (otherwise known as slow release or extended release) of such agents over a period of time effective to permit once daily administration. A well-known system for formulating such dosage forms involves a matrix comprising a hydrophilic polymer wherein the agent is dispersed; the agent is released over a period of time in the gastrointestinal tract upon dissolution or erosion of the matrix. Sustained-release dosage forms comprising such a matrix system are conveniently prepared as compressed tablets, described herein as "matrix tablets".

Drugs and prodrugs having relatively high solubility in water, for example a solubility of about 10 mg/ml or greater, present challenges to the formulator wishing to provide a sustained-release dosage form, and the higher the solubility the greater are the challenges. These challenges are well illustrated in the cases of pramipexole dihydrochloride, which has a solubility in water of about 200 mg/ml.

Pramipexole (I) is a dopamine $D_2$ receptor agonist useful in treatment of Parkinson's disease. Pramipexole as its dihydrochloride salt is commercially available in the United States as Mirapex® tablets of Pharmacia & Upjohn. These are immediate-release tablets in 0.125 mg, 0.25 mg, 0.5 mg, 1.0 mg and 1.5 mg strengths, designed for oral administration of a single tablet three times per day to provide a daily dose of 0.375 to 4.5 mg. See *Physicians' Desk Reference* 57th edition (2003), 2768-2772. Doses herein are expressed in amounts of pramipexole dihydrochloride monohydrate unless otherwise specified; 1.0 mg pramipexole dihydrochloride monohydrate is equivalent to about 0.7 mg pramipexole base.

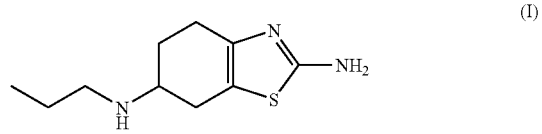

(I)

A three times daily dosing regimen for immediate-release pramipexole dihydrochloride tablets is well tolerated, but patient compliance would be much improved if a once-daily regimen were possible. In this regard, it will be noted that the primary indication for the drug, Parkinson's disease, is an affliction that becomes more prevalent with advancing age and is often accompanied by decline in memory. A once-daily regimen would be especially useful in enhancing compliance among elderly patients.

It has been found by the present inventors that formulation of pramipexole dihydrochloride in a hydrophilic matrix tablet is generally inadequate to provide sustained-release properties consistent with once-daily dosing. Release characteristics can be further modified by coating the tablet with a sustained-release coating. Such a coating typically comprises a hydrophobic polymer and a hydrophilic pore-former.

The need to provide a coating over the matrix tablet gives rise to further problems. The additional handling operations involved in a coating step require a sufficient degree of tablet hardness to avoid tablet breakage and/or attrition during these operations, particularly in a high-speed manufacturing situation.

It has proved difficult to formulate a tablet having a suitable combination of sustained-release and handling properties, where the drug is one having relatively high solubility, as in the case of pramipexole dihydrochloride.

U.S. Pat. No. 6,197,339 discloses a sustained-release tablet comprising (R)-5,6-dihydro-5-(methylamino)-4H-imidazo[4,5-ij]-quinolin-2(1H)-one (Z)-2-butenedioate (1:1) (sumanirole maleate) in a matrix comprising hydroxypropylmethylcellulose (HPMC) and starch. The tablet is disclosed to be useful in treatment of Parkinson's disease. Starches disclosed to be suitable therein include pregelatinized starch.

U.S. Pat. No. 5,458,887 discloses a controlled-release tablet comprising an osmotic core that consists of a drug in admixture with a water-swellable component such as HPMC or polyethylene oxide, and a coating that comprises a water-resistant polymer and a minor amount of a water-soluble compound that acts as a pore-former. Upon formation of pores in the coating by dissolution of the water-soluble compound, the water-swellable agent is said to expand the core and provide a drug-rich surface in contact with gastrointestinal fluid.

U.S. Pat. No. 5,656,296 discloses a dual control sustained-release formulation comprising a core that comprises a drug and a low melting point excipient, and a coating layer over the core that comprises a pH-independent water-insoluble polymer and a water-soluble film-forming polymer.

European Patent Application No. EP 0 933 079 discloses a starch said to be suitable for preparing tablets having high hardness yet being capable of rapid disintegration in an aqueous medium. Tensile strength of the finished tablets is calculated from the hardness.

Patents and publications cited above are incorporated herein by reference.

It is an object of the present invention to provide a sustained-release tablet composition of a water-soluble salt of pramipexole that is suitable for once-daily oral administration. It is a further object to provide such a composition having sufficient hardness to withstand a high-speed tableting operation, in particular to resist erosion during application of a coating layer. It is a further object to provide a pharmaceutical tablet comprising a water-soluble salt of pramipexole that provides day-long therapeutic effect when administered once daily, without substantially increased incidence of adverse side effects.

SUMMARY OF THE INVENTION

There is now provided a sustained-release pharmaceutical composition in a form of an orally deliverable tablet comprising a water-soluble salt of pramipexole, dispersed in a matrix comprising a hydrophilic polymer and a starch having a tensile strength of at least about 0.15 kN cm$^{-2}$ at a solid fraction representative of the tablet. The composition preferably exhibits sustained-release properties adequate to provide therapeutic effectiveness when administered orally not more than once daily to a subject in need thereof.

There is further provided a method of treatment of a subject having a condition or disorder for which a dopamine $D_2$ receptor agonist is indicated, the method comprising orally administering to the subject a sustained-release pharmaceutical composition in a form of a tablet comprising a water-soluble salt of pramipexole dispersed in a matrix comprising a hydrophilic polymer and a starch having a tensile strength of at least about 0.15 kN cm$^{-2}$ at a solid fraction representative of the tablet.

The term "water-soluble" herein means having solubility of at least about 10 mg/ml. Unless otherwise specified, "solubility" herein means solubility in water at 20-25° C. at any physiologically acceptable pH, for example at any pH in the range of about 4 to about 8. In the case of a salt, reference herein to solubility in water pertains to the salt, not to the free base form of pramipexole.

"Solid fraction" is the ratio of absolute to apparent density of a compact of the starch. A "compact" herein is a compressed tablet, prepared for example on a tablet press, consisting only of a sample of starch for which it is desired to measure tensile strength. A "solid fraction representative of the tablet" is a solid fraction selected to be similar to the solid fraction of tablets prepared according to the invention. Typically a solid fraction of about 0.75 to about 0.85, illustratively 0.8, will be selected.

The term "orally deliverable" herein means suitable for oral, including peroral and intra-oral (e.g., sublingual or buccal) administration, but tablets of the present invention are adapted primarily for peroral administration, i.e., for swallowing, typically whole or broken, with the aid of water or other drinkable fluid.

A "subject" herein is an animal of any species, preferably mammalian, most preferably human. Conditions and disorders in a subject for which a particular agent is said herein to be "indicated" are not restricted to conditions and disorders for which the agent has been expressly approved by a regulatory authority, but also include other conditions and disorders known or believed by a physician to be amenable to treatment with the agent. "Treatment" herein embraces prophylactic treatment unless the context requires otherwise.

DETAILED DESCRIPTION OF THE INVENTION

Figure 1:
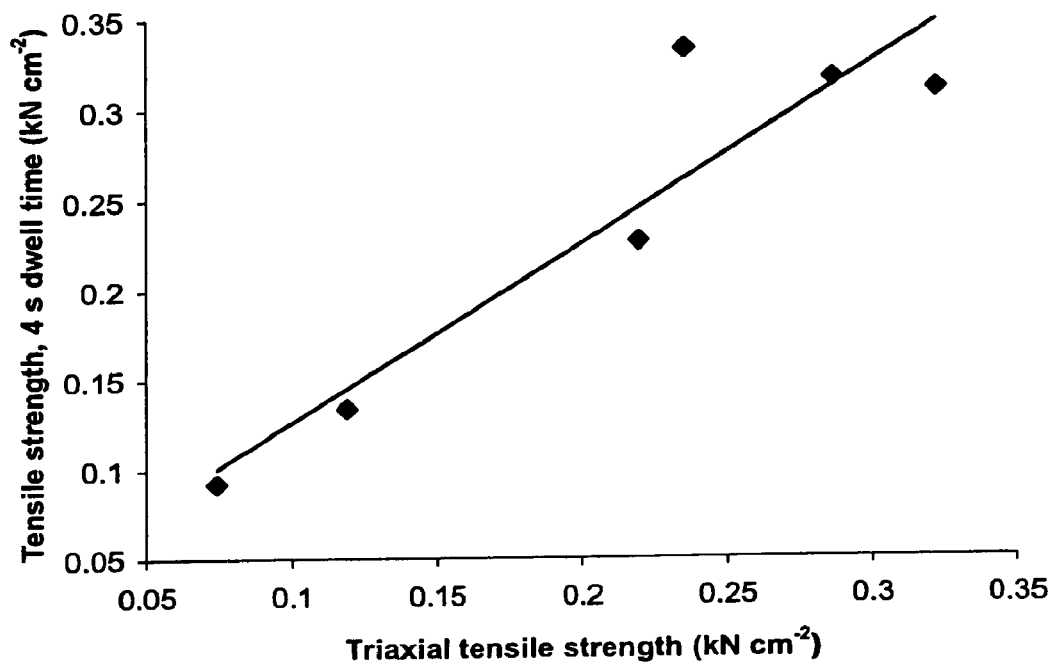
FIG. 1 is a graph showing relationship of tensile strength of pregelatinized starch lots, as determined by a test method of the invention using a 4 second dwell time (Example 1 herein) to triaxial tensile strength.

In one embodiment, the invention provides a pharmaceutical composition in a form of an orally deliverable tablet comprising a water-soluble salt of pramipexole.

Preferred salts have solubility not less than about 50 mg/ml, more preferably not less than about 100 mg/ml.

It will be understood that mention of pramipexole or a salt thereof herein embraces racemates, enantiomers, polymorphs, hydrates and solvates thereof.

Pramipexole (I) is used preferably in the form of its S-enantiomer, (S)-2-amino-4,5,6,7-tetrahydro-6-(propylamino)-benzothiazole. A preferred salt of pramipexole is the dihydrochloride salt, most preferably in the form of the monohydrate.

Pramipexole compositions of the invention are preferably suitable for administration no more than once daily. Such compositions are useful in treatment of any CNS condition or disorder for which pramipexole has therapeutic utility, but especially Parkinson's disease and complications associated therewith.

Pramipexole and its salts useful herein can be prepared by processes known per se, including processes disclosed in patents and other literature pertaining to pramipexole.

The amount of the pramipexole salt present in a composition of the invention is sufficient to provide a daily dose in one to a small plurality, for example one to about 4, of tablets to be administered at one time. Preferably the full daily dose is delivered in a single tablet.

An amount of pramipexole salt, expressed as pramipexole dihydrochloride monohydrate equivalent, of about 0.1 to about 10 mg per tablet, or about 0.05% to about 5% by weight of the composition, will generally be suitable. Preferably an amount of about 0.2 to about 6 mg, more preferably an amount of about 0.3 to about 5 mg, per tablet is present. Specific dosage amounts per tablet contemplated herein include 0.375, 0.5, 0.75, 1.0, 1.5, 3.0 and 4.5 mg pramipexole dihydrochloride monohydrate.

A composition of the present invention comprises a pramipexole salt as defined above, dispersed in a matrix comprising a hydrophilic polymer and a starch having a tensile strength of at least about 0.15 kN cm$^{-2}$ at a solid fraction representative of the tablet, for example about 0.75 to about 0.85, illustratively 0.8.

Hydrophilic polymers useful herein are pharmaceutically acceptable polymeric materials having a sufficient number and distribution of hydrophilic substituents such as hydroxy and carboxy groups to impart hydrophilic properties to the polymer as a whole. Suitable hydrophilic polymers include, without limitation, methylcellulose, HPMC (hypromellose), carmellose (carboxymethylcellulose) sodium and carbomer (polyacrylic acid). More than one such polymer can optionally be used.

HPMC is a preferred hydrophilic polymer. Various types and grades of HPMC are available. In one embodiment HPMC type 2208, preferably meeting specifications set forth in a standard pharmacopeia such as USP 24, is used. HPMC type 2208 contains 19-24% by weight methoxy and 4-12% by weight hydroxypropoxy substituents. Especially suitable HPMCs have nominal viscosity ranging from about 100 to about 10,000 mPa s; illustratively a suitable HPMC type 2208 is one having a nominal viscosity of about 4,000, with a measured viscosity of about 3,000 to about 5,600 mPa s. Such an HPMC is available, for example, as Methocel® K4MP from Dow Chemical Co., and substantially equivalent products are available from other manufacturers.

The amount of hydrophilic polymer in the composition depends on the particular polymer selected, on the active pharmaceutical agent and on the desired sustained release profile. Typically, however, the hydrophilic polymer is included in an amount of about 20% to about 70%, preferably about 30% to about 60% and more preferably about 35% to about 50%, by weight of the composition. In the illustrative case of HPMC type 2208, a suitable amount will generally be found in the range from about 30% to about 60%, preferably about 35% to about 50%, for example about 40%, by weight of the composition.

It is believed, without being bound by theory, that the hydrophilic polymer functions to provide extended or sustained release of the pramipexole, for example by gradual dissolution or erosion of the polymer in the gastrointestinal tract.

Starches useful herein include starches from any suitable botanical source, for example corn, wheat, rice, tapioca, potato, etc. Preferred starches have a relatively high ratio of amylose to amylopectin, containing for example at least about 20%, more preferably at least about 25%, amylose. Especially preferred is pregelatinized starch, which is a type of modified starch that has been processed to render the starch more flowable and directly compressible. Partially or wholly pregelatinized starches can be used.

It is believed, without being bound by theory, that the primary function of the starch in a composition of the invention is as a binding agent. A starch meeting the tensile strength criterion defined herein can be referred to as a "super binder".

The amount of starch in the composition is typically higher than is conventionally present as a binder in tablet formulations. Suitable amounts will generally be found in the range of about 25% to about 75% by weight. Preferably the amount of starch is about 40% to about 70%, more preferably about 45% to about 65%, for example about 50%, by weight of the composition.

Tensile strength of a starch sample can be measured by any suitable test. Illustrative test procedures are described by Hiestand & Smith (1984), *Powder Technology* 38, 145-159, and by Hiestand & Smith (1991), *International Journal of Pharmaceutics* 67, 231-246, these articles being incorporated herein by reference.

An example of a tensile strength test that can be used (herein referred to as a "triaxial tensile strength test") requires preparation of a series of compacts of the starch sample, followed by determination of tensile strength of the compacts using a computerized multifunction tablet tester (MTT). The compacts are prepared with various degrees of compression force to provide compacts having a range of solid fraction. As a sustained release tablet formulation typically has a solid fraction of about 0.8, it is useful to prepare compacts approximating such a solid fraction.

Absolute density of the starch sample can be determined using a helium-air pycnometer.

A computer-controlled triaxial tablet press is used to prepare the compacts. Voltage output from the punch and die load cells of the tablet press are first zeroed. The punch and die are lubricated with magnesium stearate powder and the die assembly is placed in the press. Compression and decompression parameters are selected on the computer. The desired amount of starch to be compacted is weighed and poured into the die cavity. The resulting powder bed is leveled with a spatula. The punch is inserted into the die and the computer-controlled compression/decompression cycle is started.

Just prior to the end of the compression phase, thickness of the compact as measured by LVDT (linear variable differential transformer) is recorded. At the end of the compression phase, the final compression force as measured by voltage of the punch load cell is recorded.

At the end of the decompression phase, the punch and die rams are retracted. The compact is removed from the die and inspected for defects, such as cracking or sticking. Cracking can be reduced by increasing decompression time. If the compact is free of defects, its length, width, thickness and weight are measured to enable calculation of apparent density. Solid fraction is calculated by dividing absolute density by apparent density.

In preparation of the MTT for tensile strength determination, a suitable software program is run. The platen is screwed to the load cell of the MTT and the tensile strength assembly is slid into the MTT opposite the platen. The load cell signal is monitored via the computer and the zero offset on the signal conditioner is adjusted to provide a positive baseline voltage as close as possible to zero. A forward velocity is selected that will generate a time constant of approximately 15 seconds (usually the velocity selected will be about 0.8 to about 1.2 mm s$^{-1}$).

The compact to be tested is placed in the holder of the tensile strength assembly. The motor is initiated via the computer, driving the platen toward the compact until the surface of the compact is detected, and stopping the platen a few millimeters from the compact. The oscilloscope is triggered, to record the force applied to the compact, and the motor is restarted. The platen is driven into the compact until a crack is detected, either by sight or by sound, and the motor is immediately reversed.

Peak force is recorded from the oscilloscope trace. Tensile strength is calculated from the peak force using appropriate computer software.

From several runs using compacts at a range of solid fractions around 0.8, data are plotted and tensile strength at a solid fraction of 0.8 is estimated. If the tensile strength at a solid fraction of 0.8 is about 0.15 kN cm$^{-2}$ or greater, the starch sample is deemed to be suitable for use in preparing a composition according to the invention.

It has now surprisingly been discovered that a much simpler test, one that is more amenable to implementation in a manufacturing setting, can be used to estimate tensile strength of a starch sample, in particular to determine whether the starch sample has a tensile strength of at least about 0.15 kN cm$^{-2}$ at a solid fraction representative of a desired sustained-release tablet.

According to this test, compacts of the starch sample are prepared on a standard automated tablet press under a range of compression forces. For example, a Carver press (e.g., Model 3888.1DT0000) fitted with flat-faced tooling of suitable diameter (e.g., $^{10}/_{32}$ inch or about 0.7 cm for a 300 mg compact), operated at compression forces of about 4 to about 16 kN (about 900 to about 3600 lbf) for a dwell time of at least about 4 seconds has been found to give satisfactory results. Illustratively, such compacts can be prepared at 1000, 1500, 2000 and 3000 lbf (4.45, 6.67, 8.90 and 13.34 kN). Preferably a dwell time of at least about 10 seconds, more preferably at least about 30 seconds, still more preferably at least about 60 seconds, is used. Illustratively, a dwell time of 90 seconds has been found to give satisfactory results. Weight, diameter and thickness of each compact are measured accurately (alternatively, diameter can be assumed to equal that of the tooling) to enable calculation of apparent density and hence solid fraction, absolute density having been measured as described above, for example by helium-air pycnometry.

Hardness of each compact thus prepared is then determined by any suitable tablet hardness test, for example using a Key HT 500 hardness tester. Hardness is a measure of the force required to cause crushing of the compact, and is typically expressed in units such as kiloponds (kp) or Strong-Cobb units (SCU). A hardness of about 10.2 kp or about 14.4 SCU corresponds to a force of 0.1 kN.

For present purposes it is considered that crushing strength of the compact is equivalent to tensile strength. Thus tensile strength ($\sigma_T$, in kN cm$^{-2}$) can be calculated from the equation $$\sigma_T = 2F/\pi DH$$

where F is the force required to cause crushing (in kN), D is diameter of the compact (in cm) and H is thickness of the compact (in cm). For example, a compact of diameter 0.7 cm and thickness 0.4 cm having a hardness of 20 SCU (equivalent to a force of 0.139 kN) has a calculated tensile strength of 0.316 kN cm$^{-2}$.

The relationship between tensile strength and solid fraction is next established for the starch sample. This can be done by plotting data for tensile strength and solid fraction on a graph (solid fraction tends to increase with increasing compression force during preparation of the compact) or by performing a regression analysis. From that relationship, tensile strength at a standardized value of solid fraction can be estimated. The standardized value selected is one that is representative of the solid fraction of a desired sustained-release tablet, e.g., 0.8.

Where the material of the compact is pregelatinized starch, it has been found that tensile strength as determined in a simple test as described immediately above is surprisingly close to a "true" tensile strength measurement as determined by the triaxial tensile strength test method previously described, which in turn is essentially similar to methods known in the art such as that disclosed by Hiestand & Smith (1984), op. cit.

It has also been found that a longer dwell time (e.g., 90 seconds) in the test method of the present invention gives a better correlation with triaxial tensile strength than a very short dwell time (e.g., 4 seconds). See Example 1 below and FIGS. 1 and 2.

An especially preferred starch has a tensile strength of at least about 0.175 kN cm$^{-2}$, even more preferably at least about 0.2 kN cm$^{-2}$, at a solid fraction representative of a desired sustained-release tablet.

Even among commercially available pregelatinized starches, the preferred type of starch for use in a composition of the invention, considerable variation exists in tensile strength. Pregelatinized starches not meeting the tensile strength criterion established herein are not readily identified without testing, for example by a method as disclosed above. Such pregelatinized starches are generally unsuitable for commercial-scale manufacture of a sustained-release matrix tablet formulation of a water-soluble drug or prodrug, because of a problem as set forth immediately below.

An uncoated tablet, or a tablet core prior to coating, comprising starch and a hydrophilic polymer acting as a matrix for a water-soluble drug or prodrug requires to have a certain minimum hardness in order to be able to resist breakage and/or attrition due to mechanical stresses imposed during a high-speed tableting operation (including all steps up to and including filling of the tablets into containers). The minimum acceptable hardness will depend on a number of factors, including the severity of the mechanical stresses, but is typically at least about 20 SCU, preferably at least about 22 SCU, more preferably at least about 24 SCU (about 17 kp).

Figure 3:
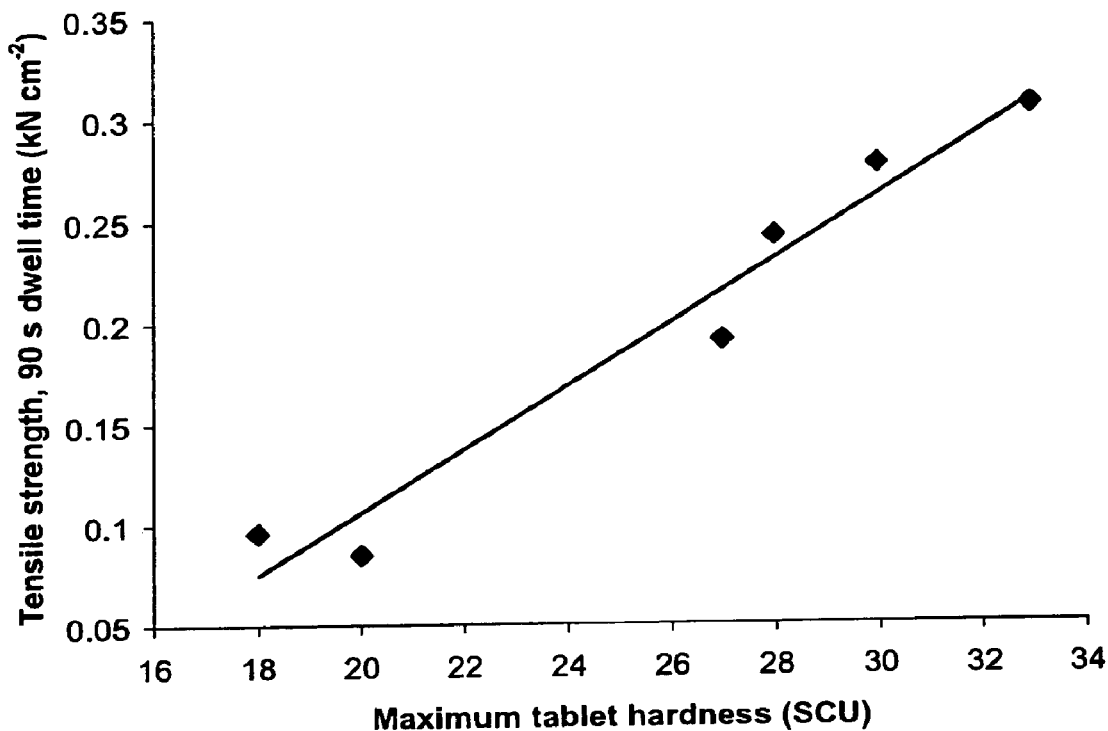
FIG. 3 is a graph showing correlation of tensile strength of pregelatinized starch lots with maximum hardness of tablets containing these lots.

Hardness can be increased by increasing the compression force applied by the tablet press, but only up to a certain level. At least in the case of tablets as described herein, above a certain compression force, further increases in compression force give little or no further increase in tablet hardness. There is, in other words, a maximum hardness achievable by compression of a particular starch/hydrophilic polymer/active agent composition. A starch providing a maximum hardness inadequate to withstand the mechanical stresses of a high-speed tableting operation is unsuitable for the present purpose. As shown in FIG. 3, certain pregelatinized starches have been found to provide a maximum hardness of 20 SCU or less; these are now identified as starches having low tensile strength (0.1 kN cm$^{-2}$ or less according to the test method of the invention utilizing a dwell time of 90 seconds).

Even if a maximum hardness of at least about 20 SCU is achievable, with a starch of low tensile strength it may be achievable only by use of extremely high compression forces. A requirement for such forces reduces speed and efficiency and increases cost of a tableting operation and is undesirable for these reasons.

Where tablets are to be subjected to an additional process step after compression, in particular a coating step, exposure to mechanical stresses is greatly increased. According to a preferred embodiment, therefore, the sustained-release tablet of the invention further comprises a coating.

For pramipexole salts of high water solubility as specified herein, a hydrophilic polymer matrix can be inadequate to provide sustained release of sufficiently long duration to permit once daily administration. It is believed that such salts are readily leached out of the hydrophilic matrix when contacted by an aqueous medium such as gastrointestinal fluid. It is therefore desirable to further slow the process of drug release by providing a release-controlling coating around the tablet. Such a coating typically comprises a hydrophobic or water-insoluble polymer component such as ethylcellulose together with a hydrophilic or water-soluble pore-forming component such as HPMC.

Where a starch is used having a tensile strength of at least about 0.15 kN cm$^{-2}$, preferably at least about 0.175 kN cm$^{-2}$, more preferably at least about 0.2 kN cm$^{-2}$, at a solid fraction representative of the tablet (e.g., about 0.75 to about 0.85), the composition is found to be especially suited to a high-speed tableting operation that includes a step of coating the tablet with a release-controlling layer.

Alternatives to ethylcellulose and HPMC as components of a release coating layer include other cellulosic polymers (e.g., methylcellulose, hydroxypropylcellulose, hydroxyethylcellulose, carboxymethylcellulose sodium, cellulose esters such as cellulose acetate, etc.), polyvinyl acetate, polyvinyl pyrrolidone, polymers and copolymers of acrylic acid and methacrylic acid and esters thereof, polyethylene glycol, carrageenan and other gums, and the like.

A release-controlling layer, if present, typically constitutes about 1% to about 15%, preferably about 2.5% to about 10%, by weight of the tablet as a whole. The hydrophobic or water-insoluble component, preferably comprising ethylcellulose, typically constitutes about 1% to about 10%, preferably about 2% to about 7%, by weight of the tablet as a whole. The pore-forming component, preferably comprising HPMC, is typically present in an amount of about 5% to about 50%, preferably about 10% to about 40%, by weight of the water-insoluble or hydrophobic component.

The coating, if present, can optionally contain additional pharmaceutically acceptable excipients such as plasticizers, dyes, etc.

Illustratively, a release-controlling layer in an amount of about 2.5% to about 5% by weight of the tablet core (i.e., the tablet weight excluding the coating) comprises an ethylcellulose-based material (e.g., Surelease® of Colorcon) and an HPMC-based pore-forming material (e.g., Opadry® of Colorcon) in a weight ratio of about 3:1 to about 4:1.

A release-controlling layer or coating should be applied at as uniform a thickness as possible to provide optimum control of release rate of the pramipexole.

Alternatively or in addition, the sustained-release tablet of the invention comprises a nonfunctional coating. A nonfunctional coating can comprise a polymer component, for example HPMC, optionally with other ingredients, for example one or more plasticizers, colorants, etc. The term "nonfunctional" in the present context means having no substantial effect on release properties of the tablet, and does not imply that the coating serves no useful purpose. For example, such a coating can impart a distinctive appearance to the tablet, provide protection against attrition during packaging and transportation, improve ease of swallowing, and/or have other benefits. A nonfunctional coating should be applied in an amount sufficient to provide complete coverage of the tablet. Typically an amount of about 1% to about 10%, more typically an amount of about 2.5% to about 5%, by weight of the tablet as a whole, will be found suitable.

Uncoated tablets and cores of coated tablets of the invention can optionally contain one or more pharmaceutically acceptable excipients in addition to the starch and hydrophilic polymer components described above. Such excipients include without limitation glidants and lubricants. Other conventional excipients known in the art can also be included.

A glidant can be used to improve powder flow properties prior to and during tableting and to reduce caking. Suitable glidants include colloidal silicon dioxide, magnesium trisilicate, powdered cellulose, starch, talc, tribasic calcium phosphate and the like. In one embodiment, colloidal silicon dioxide is included as a glidant in an amount up to about 2%, preferably about 0.2% to about 0.6%, by weight of the tablet.

A lubricant can be used to enhance release of a tablet from apparatus on which it is formed, for example by preventing adherence to the face of an upper punch ("picking") or lower punch ("sticking"). Suitable lubricants include magnesium stearate, calcium stearate, canola oil, glyceryl palmitostearate, hydrogenated vegetable oil, magnesium oxide, mineral oil, poloxamer, polyethylene glycol, polyvinyl alcohol, sodium benzoate, sodium lauryl sulfate, sodium stearyl fumarate, stearic acid, talc, hydrogenated vegetable oil, zinc stearate and the like. In one embodiment, magnesium stearate is included as a lubricant in an amount of about 0.1% to about 1.5%, preferably about 0.3% to about 1%, by weight of the tablet.

Tablets can be of any suitable size and shape, for example round, oval, polygonal or pillow-shaped, and optionally bear nonfunctional surface markings. Especially in the case of coated tablets they are preferably designed to be swallowed whole and are therefore typically not provided with a breaking score. Tablets of the invention can be packaged in a container, accompanied by a package insert providing pertinent information such as, for example, dosage and administration information, contraindications, precautions, drug interactions and adverse reactions.

There is also provided a method of treatment of a subject having a condition or disorder for which a dopamine $D_2$ receptor agonist is indicated, the method comprising orally administering to the subject a sustained-release pharmaceutical composition in a form of a tablet comprising a water-soluble salt of pramipexole dispersed in a matrix comprising a hydrophilic polymer and a starch having a tensile strength of at least about 0.15 kN cm$^{-2}$ at a solid fraction representative of the tablet. Preferably the composition is administered no more than once daily.

In a particular embodiment, the condition or disorder is Parkinson's disease or a complication associated therewith.

Suitable daily dosage amounts include 0.375, 0.5, 0.75, 1.0, 1.5, 3.0 and 4.5 mg pramipexole dihydrochloride monohydrate.

In a further embodiment, a composition of the invention is administered in combination therapy with one or more additional drugs or prodrugs. The term "combination therapy" herein means a treatment regimen wherein the agent provided by the composition of the invention and a second agent are administered individually or together, sequentially or simultaneously, in such a way as to provide a beneficial effect from co-action of these therapeutic agents. Such beneficial effect can include, but is not limited to, pharmacokinetic or pharmacodynamic co-action of the therapeutic agents. Combination therapy can, for example, enable administration of a lower dose of one or both agents than would normally be administered during monotherapy, thus decreasing risk or incidence of adverse effects associated with higher doses. Alternatively, combination therapy can result in increased therapeutic effect at the normal dose of each agent in monotherapy. "Combination therapy" herein is not intended to encompass administration of two or more therapeutic agents as part of separate monotherapy regimens that incidentally and arbitrarily result in sequential or simultaneous treatment.

Compositions of the invention can be especially suited to combination therapies, particularly where the second agent is one that is, or can be, administered once daily. There are significant advantages in patient convenience and compliance where both components of a combination therapy can be administered at the same time and with the same frequency. This is especially true in the case of geriatric patients or those suffering memory impairment.

When administered simultaneously, the two components of the combination therapy can be administered in separate dosage forms or in coformulation, i.e., in a single dosage form. When administered sequentially or in separate dosage forms, the second agent can be administered by any suitable route and in any pharmaceutically acceptable dosage form, for example by a route and/or in a dosage form other than the present composition. In a preferred embodiment, both components of the combination therapy are formulated together in a single dosage form.

EXAMPLES

Example 1

Tensile strength of six commercially obtained lots of pregelatinized starch was determined using the triaxial tensile strength test procedure described hereinabove. Data for tensile strength at a solid fraction of 0.8 are presented in Table 1.

TABLE 1

Tensile strength of pregelatinized starch lots at a solid fraction of 0.8 (triaxial test procedure)

| Lot | Tensile strength (kN cm$^{-2}$) |
|---|---|
| 1 | 0.323 |
| 2 | 0.220 |
| 3 | 0.074 |
| 4 | 0.119 |
| 5 | 0.287 |
| 6 | 0.236 |

A great variation in tensile strength of pregelatinized starches was observed, ranging from 0.074 to 0.323 kN cm$^{-2}$. Lots 3 and 4, exhibiting the lowest values of tensile strength, were from one manufacturer. Lots 1, 5 and 6, exhibiting the highest values of tensile strength, were from a second manufacturer. Lot 2, exhibiting an intermediate value of tensile strength, was from a third manufacturer.

Example 2

Tensile strength of the same six lots of pregelatinized starch was determined by the following simplified test procedure.

Compacts of each starch lot were prepared on a Carver press, Model 3888.1DT0000 fitted with ¹⁹⁄₃₂ inch (0.7 cm) flat-faced tooling, at compression forces of 1000, 1500, 2000 and 3000 lbf (4.45, 6.67, 8.90 and 13.34 kN), for a dwell time of 4 seconds or 90 seconds. Compacts of an additional three lots of pregelatinized starch (Lots 7, 8 and 9), from the same manufacturer as Lots 3 and 4, were prepared using a dwell time of 90 seconds only. Weight and thickness of each compact was measured (diameter being equal to that of the tooling) to enable calculation of apparent density. Absolute density of each starch lot was measured by helium-air pycnometry. Solid fraction was calculated as the ratio of apparent to absolute density.

Hardness (force required to cause crushing) of each compact was determined using a Key HT 500 hardness tester. Tensile strength was calculated from this force and dimensions of the compact, using the equation $\sigma_T = 2F/\pi DH$ as described hereinabove.

A regression analysis was performed to determine the relationship of tensile strength to solid fraction for each starch lot, and tensile strength at a standardized solid fraction of 0.8 was calculated. Data are presented in Table 2.

TABLE 2

Tensile strength of pregelatinized starch lots at a solid fraction of 0.8 (simplified test procedure of the invention)

| | Tensile strength (kN cm$^{-2}$) | |
|---|---|---|
| Lot | 4 s dwell time | 90 s dwell time |
| 1 | 0.310 | 0.306 |
| 2 | 0.227 | 0.191 |
| 3 | 0.092 | 0.085 |
| 4 | 0.134 | 0.096 |
| 5 | 0.316 | 0.277 |
| 6 | 0.333 | 0.242 |
| 7 | n.d. | 0.087 |
| 8 | n.d. | 0.088 |
| 9 | n.d. | 0.172 |

Correlation of tensile strength as measured in the simplified test using a 4 second dwell time (this Example) with tensile strength as measured by the triaxial test procedure of Example 1 is shown graphically in FIG. 1.

Figure 2:
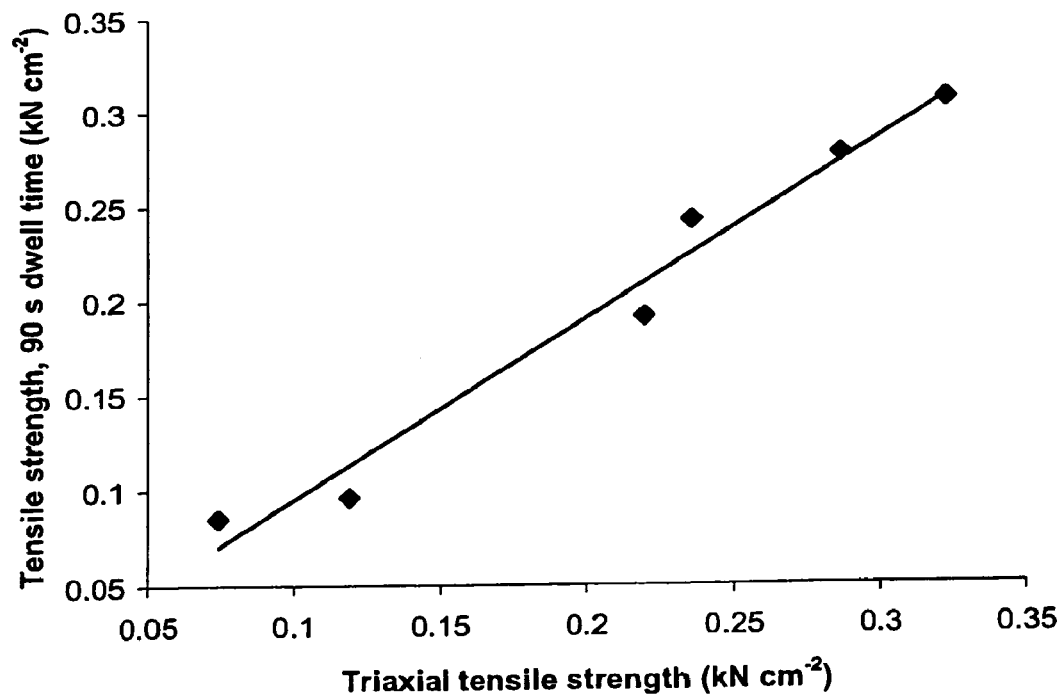
FIG. 2 is a graph showing relationship of tensile strength of pregelatinized starch lots, as determined by a test method of the invention using a 90 second dwell time (Example 1 herein) to triaxial tensile strength.

Correlation of tensile strength as measured in the simplified test using a 90 second dwell time (this Example) with tensile strength as measured by the triaxial test procedure of Example 1 is shown graphically in FIG. 2.

Both dwell times exhibited a strong correlation, but the correlation was especially close where the simplified test used a 90 second dwell time. It is concluded that the simplified test as herein described can be used to estimate tensile strength of a starch lot for the purpose of predicting whether that starch lot will be suitable for preparing a sustained-release tablet formulation of the present invention.

Example 3

Sumanirole maleate sustained-release tablets were prepared having the compositions shown in Table 3. Tablet strength in mg is expressed as sumanirole base.

TABLE 3

Composition of sumanirole maleate tablets of Example 3

| | Tablet strength (mg) | | | | | | | |
|---|---|---|---|---|---|---|---|---|
| | 0.5 | 1 | 2 | 4 | 8 | 8 | 12 | 24 |
| Ingredient | Amount (% by weight) | | | | | | | |
| sumanirole maleate | 0.23 | 0.45 | 0.9 | 1.8 | 3.6 | 3.6 | 5.4 | 10.9 |
| HPMC type 2208, 4000 mPa s | 35.00 | 35.00 | 35.0 | 35.0 | 35.0 | 35.0 | 35.0 | 35.0 |
| pregelatinized starch | 63.87 | 63.65 | 63.2 | 62.3 | 60.5 | 60.0 | 58.2 | 52.5 |
| colloidal silicon dioxide | 0.40 | 0.40 | 0.4 | 0.4 | 0.4 | 0.4 | 0.4 | 0.4 |
| magnesium stearate | 0.50 | 0.50 | 0.5 | 0.5 | 0.5 | 1.0 | 1.0 | 1.0 |

All ingredients except the lubricant (magnesium stearate) were screened to remove lumps and were blended thoroughly in a low-shear mixer operating at 24 rpm for 10-30 minutes. The lubricant was then screened into the mixer and the materials were blended for a further 2-5 minutes. The resulting lubricated mixture was compressed into 350 mg pillow-shaped tablets using a Kilian S100 tableting machine.

Example 4

Tablets similar to those of Example 3 were prepared using pregelatinized starches of lots 1-6 as tested in Examples 1 and 2. Maximum hardness of the tablets obtainable with each pregelatinized starch lot was determined.

Maximum hardness was correlated with tensile strength of the pregelatinized starch lot used, as measured in the simplified test of Example 2 using a 90 second dwell time. Results are shown in FIG. 3. The correlation was substantially linear.

In subsequent tests, tablets of different hardness were used as cores for coating and were tested for resistance to erosion during a high-speed coating operation. Tablet cores having a hardness of at least about 24 SCU (about 17 kp) were found to have acceptable resistance to erosion. As shown in FIG. 3, this degree of hardness is achievable using pregelatinized starch having a tensile strength of at least about $0.175$ kN cm$^{-2}$. Pregelatinized starches of Lots 3 and 4 were unsuitable, having tensile strength less than about $0.15$ kN cm$^{-2}$ and providing tablets having a maximum hardness no greater than about 20 SCU (about 14 kp).

Example 5

Pramipexole dihydrochloride sustained-release tablets were prepared having the compositions shown in Table 4.

TABLE 4

Composition of pramipexole dihydrochloride tablets of Example 5

| Ingredient | Amount (mg) | | | | | | | |
|---|---|---|---|---|---|---|---|---|
| pramipexole dihydrochloride monohydrate | 0.375 | 0.75 | 1.5 | 3.0 | 4.5 | 0.375 | 0.375 | 4.5 |
| HPMC type 2208, 4000 mPa s | 140.0 | 140.0 | 140.0 | 140.0 | 140.0 | 70.0 | 157.5 | 157.5 |
| pregelatinized starch | 206.5 | 206.1 | 205.4 | 203.9 | 202.4 | 101.5 | 189.0 | 184.9 |
| colloidal silicon dioxide | 1.4 | 1.4 | 1.4 | 1.4 | 1.4 | 1.4 | 1.4 | 1.4 |
| magnesium stearate | 1.75 | 1.75 | 1.75 | 1.75 | 1.75 | 1.75 | 1.75 | 1.75 |
| total | 350 | 350 | 350 | 350 | 350 | 175 | 350 | 350 |

The tablets were prepared by the procedure described in Example 3, using pregelatinized starch having a tensile strength of at least about $0.175$ kN cm$^{-2}$.

Example 6

Coated sustained-release tablets of pramipexole dihydrochloride were prepared having the composition shown in Table 5.

TABLE 5

Composition of coated tablets of Example 6

| Ingredient | Amount (mg) |
|---|---|
| pramipexole dihydrochloride monohydrate | 0.375 |
| HPMC type 2208, 4000 mPa s | 140.0 |
| pregelatinized starch | 206.5 |
| colloidal silicon dioxide | 1.4 |
| magnesium stearate | 1.75 |
| total core | 350 |
| ethylcellulose-based coating material (Surelease ®) | 7.88 |
| HPMC-based coating material (Opadry ®) | 2.63 |
| total coating | 10.5 |

Tablet cores were prepared exactly as in Example 5, using pregelatinized starch having a tensile strength of at least about $0.175$ kN cm$^{-2}$. A coating solution was prepared as follows. Opadry® HPMC-based material in an amount of 6.004 g was added to 106.682 g water and mixed for 45 minutes to provide an HPMC mixture. Next, 72.045 g Surelease® ethylcellulose-based material was added to the HPMC mixture and mixed for an additional 30 minutes to provide a coating solution.

The coating solution was applied to the tablet cores in an amount providing a 3% weight gain. The resulting coated tablets were cured using a 12 inch (about 30 cm) Vector LCDS or 24 inch (about 60 cm) Thomas Accela-Coata coating pan for about 15 minutes at a bed temperature of at least about 70° C. After curing, temperature was ramped down over a period of about 8 minutes to an exhaust temperature of about 45° C.

Example 7

Coated sustained-release tablets of pramipexole dihydrochloride were prepared having the composition shown in Table 6.

TABLE 6

Composition of coated tablets of Example 7

| Ingredient | Amount (mg) |
|---|---|
| pramipexole dihydrochloride monohydrate | 0.375 |
| HPMC type 2208, 4000 mPa s | 140.0 |
| pregelatinized starch | 206.5 |
| colloidal silicon dioxide | 1.4 |
| magnesium stearate | 1.75 |
| total core | 350 |
| ethylcellulose-based coating material (Surelease ®) | 8.4 |
| HPMC-based coating material (Opadry ®) | 2.1 |
| total coating | 10.5 |

Tablet cores were prepared exactly as in Example 5, using pregelatinized starch having a tensile strength of at least about $0.175$ kN cm$^{-2}$. A coating solution was prepared as follows. Opadry® HPMC-based material in an amount of 4.801 g was added to 103.041 g water and mixed for 45 minutes to provide an HPMC mixture. Next, 76.819 g Surelease® ethylcellulose-based material was added to the HPMC mixture and mixed for an additional 30 minutes to provide a coating solution.

Coating to a 3% weight gain and curing of the coated tablets were performed exactly as in Example 6.

Example 8

Coated sustained-release tablets of pramipexole dihydrochloride were prepared having the composition shown in Table 7.

TABLE 7

Composition of coated tablets of Example 8

| Ingredient | Amount (mg) |
| --- | --- |
| pramipexole dihydrochloride monohydrate | 0.375 |
| HPMC type 2208, 4000 mPa s | 140.0 |
| pregelatinized starch | 206.5 |
| colloidal silicon dioxide | 1.4 |
| magnesium stearate | 1.75 |
| total core | 350 |
| ethylcellulose-based coating material (Surelease ®) | 13.13 |
| HPMC-based coating material (Opadry ®) | 4.38 |
| total coating | 17.5 |

Tablet cores were prepared exactly as in Example 5, using pregelatinized starch having a tensile strength of at least about 0.175 kN cm$^{-2}$. A coating solution was prepared as follows. Opadry® HPMC-based material in an amount of 10.003 g was added to 177.737 g water and mixed for 45 minutes to provide an HPMC mixture. Next, 120.03 g Surelease® ethylcellulose-based material was added to the HPMC mixture and mixed for an additional 30 minutes to provide a coating solution.

Coating to a 3% weight gain and curing of the coated tablets were performed exactly as in Example 6. After this first curing step, coating was repeated to provide a total tablet weight gain of about 5%, followed by curing for about 15 minutes at a bed temperature of at least about 70° C. After curing, temperature was ramped down over a period of about 8 minutes to an exhaust temperature of about 45° C.

Example 9

Coated sustained-release tablets of pramipexole dihydrochloride were prepared having the composition shown in Table 8.

TABLE 8

Composition of coated tablets of Example 9

| Ingredient | Amount (mg) |
| --- | --- |
| pramipexole dihydrochloride monohydrate | 0.375 |
| HPMC type 2208, 4000 mPa s | 140.0 |
| pregelatinized starch | 206.5 |
| colloidal silicon dioxide | 1.4 |
| magnesium stearate | 1.75 |
| total core | 350 |
| ethylcellulose-based coating material (Surelease ®) | 14.0 |
| HPMC-based coating material (Opadry ®) | 3.5 |
| total coating | 17.5 |

Tablet cores were prepared exactly as in Example 5, using pregelatinized starch having a tensile strength of at least about 0.175 kN cm$^{-2}$. A coating solution was prepared as follows. Opadry® HPMC-based material in an amount of 8.002 g was added to 171.735 g water and mixed for 45 minutes to provide an HPMC mixture. Next, 128.032 g Surelease® ethylcellulose-based material was added to the HPMC mixture and mixed for an additional 30 minutes to provide a coating solution.

Coating to a 5% total weight gain and curing of the coated tablets were performed exactly as in Example 8.

Example 10

Dissolution profiles of the 0.375 mg pramipexole dihydrochloride tablets of each of Examples 5, 6 and 9 were evaluated in a standard in vitro USP dissolution assay under the following conditions. USP apparatus 1 was used to stir a dissolution medium (900 ml of 0.05M phosphate buffer at a pH of 6.8) at a spindle rotation speed of 100 rpm and a temperature of 37° C.

Figure 4:
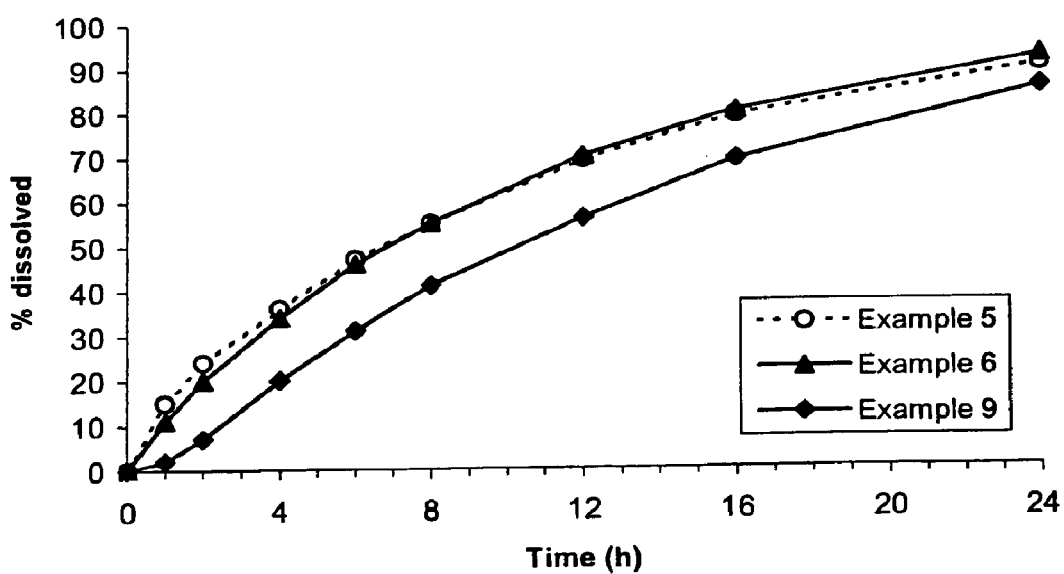
FIG. 4 is a graph showing in vitro dissolution profiles of three different 0.375 mg sustained-release tablet formulations of pramipexole dihydrochloride monohydrate, as more fully described in Example 10.

Data are shown in FIG. 4. The uncoated tablet of Example 5 and the tablet of Example 6 having a 3% coating comprising 25% pore-former exhibited very similar overall dissolution profiles. On close inspection, however, it will be noticed that the uncoated tablet of Example 5 showed faster initial dissolution, such that at 1 hour and 2 hour sampling times the percent dissolved was greater, than in the case of the coated tablet of Example 6. For example, at 1 hour, the coated tablet of Example 6 showed only 11% dissolution, while the uncoated tablet of Example 5 showed 15% dissolution. Similarly, at 2 hours, the coated tablet of Example 6 showed no more than 20% dissolution, while the uncoated tablet of Example 5 showed 24% dissolution.

Dissolution of the tablet of Example 9 having a 5% coating comprising 20% pore-former exhibited a dissolution profile much slower than either the tablet of Example 5 or the tablet of Example 6.

Example 11

An in vivo study was conducted in healthy human volunteers to assess bioavailability of pramipexole formulated as the 0.375 mg sustained-release or extended-release (XR) tablets of Examples 5, 6 and 9 by comparison with a reference treatment with immediate-release (IR) pramipexole dihydrochloride tablets, and to evaluate safety of pramipexole when its absorption profile is altered as in these extended-release tablets.

Method

The study followed an open-label, 4-way, randomized crossover design and was conducted in healthy male and female subjects ranging from 18 to 55 years of age. The subjects received each of the four treatments during the course of the study, which was conducted at a single center. A total of 12 subjects were enrolled. The subjects were fasted overnight and then given a 0.375 mg oral dose of pramipexole dihydrochloride monohydrate. In the case of the IR formulation, which was provided as Mirapex® tablets, three equally divided doses of 0.125 mg each were given at 8-hour intervals, beginning in the morning. In the case of the XR formulations of Examples 5, 6 and 9, a single 0.375 mg tablet was given in the morning. Serial blood samples were taken over a 48-hour period for PK assessment. Adverse events were recorded during the same 48-hour period.

Plasma pramipexole concentrations were quantitated by an HPLC-MS/MS method, validated over the assay range 0.05-15 ng/ml. All runs met bioanalytical acceptance criteria for calibration standards and quality control. Samples were not diluted prior to analysis as all sample concentrations were within the limits of quantitation.

PK parameters for pramipexole were estimated by non-compartmental methods, using the nonlinear regression program Kinetica of Innaphase. Individual plasma concentration data and the actual time-points of blood sampling from each subject were used in the analysis. Plasma concentrations below the lower limit of quantitation at early time-points were set to zero, whereas those in the terminal phase were excluded from the analysis.

In vivo pramipexole absorption data were derived by a deconvolution routine employing the Kinetica program. To perform this analysis, a fit of the pramipexole data from the reference treatment was first made to a one-compartment open PK disposition model with first order absorption. Based on this fit, plasma pramipexole concentrations were simulated for a 0.375 mg intravenous bolus dose of pramipexole. These simulated pramipexole concentrations were used in the deconvolution routine.

In vitro/in vivo correlations for each of the pramipexole XR formulations were examined by evaluating a linear relationship of in vivo absorption as a function of in vitro dissolution.

Prediction of mean steady-state concentrations arising from repeated daily dosing was performed by interpolation of hourly concentrations from individual subjects' observed concentration/time data and then by the principle of superposition, estimating the concentrations during the 6th day of dosing. Estimates of half-life obtained from this study, which were consistent with values reported previously, indicate that steady-state would be achieved by the 4th day. The steady-state parameters $T_{max}$, $C_{max}$, $C_{min}$, $AUC_{0-\tau}$, $C_{avg}$ (calculated as $AUC_{0-24}/\tau$) and FR (fluctuation ratio, calculated as $(C_{max}-C_{min})/C_{avg}$) were also estimated during this exercise.

Results

Of the 12 subjects enrolled, 10 completed the study. Two subjects were dropped prior to receiving the reference treatment, therefore their data were not included in the PK analysis.

Figure 5:
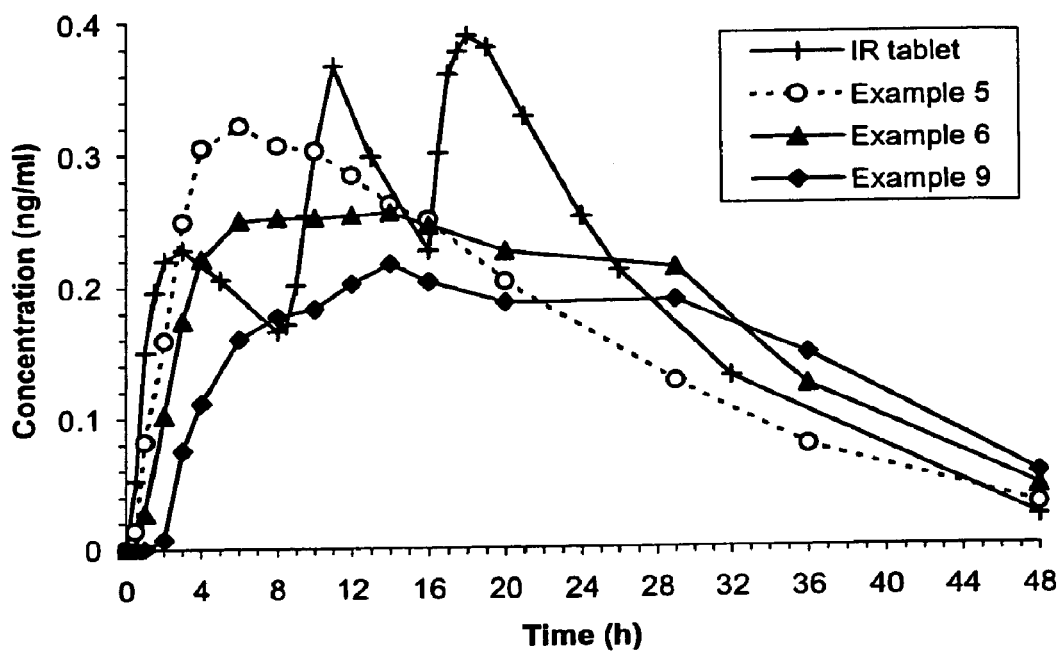
FIG. 5 is a graph from a human PK study showing time course of mean plasma pramipexole concentration following oral administration of 0.375 mg pramipexole dihydrochloride, either as a 0.125 mg immediate-release tablets administered three times at 8-hour intervals or as a single 0.375 mg dose of each of three different sustained-release tablets, as more fully described in Example 10.

Mean plasma pramipexole concentrations over the 48-hour assessment period are shown in FIG. 5. PK estimates derived from the individual subject data are provided in Table 9.

TABLE 9

PK parameters (mean ± standard deviation)

| Parameter | IR tablet (Mirapex ®) | XR tablets | | |
|---|---|---|---|---|
| | | Example 5 | Example 6 | Example 9 |
| $AUC_{0-\infty}$ (ng · h/ml) | 9.93 ± 3.05 | 9.05 ± 3.24 | 9.66 ± 2.91 | 8.91 ± 4.15 |
| $AUC_{0-48}$ (ng · h/ml) | 8.60 ± 2.63 | 7.76 ± 2.83 | 7.60 ± 2.00 | 7.07 ± 2.77 |
| $C_{max}$ (ng/ml) | 0.433 ± 0.083* | 0.332 ± 0.076 | 0.282 ± 0.069 | 0.242 ± 0.062 |
| $T_{max}$ (h) | 15.9 ± 3.4* | 6.2 ± 2.0 | 12.0 ± 5.3 | 15.6 ± 6.2 |
| $T_{1/2}$ (h) | 9.1 ± 2.6 | 11.4 ± 4.1 | 11.9 ± 2.8 | 12.1 ± 6.0 |

*reached after third 0.125 mg tablet

Mean cumulative absorption data (up to 24 hours) for the XR tablets are shown in Table 10, together with corresponding in vitro dissolution data from Example 10.

TABLE 10

In vitro dissolution and in vivo absorption data for XR tablets

| | Example 5 | | Example 6 | | Example 9 | |
|---|---|---|---|---|---|---|
| Time (h) | % diss. (in vitro) | % abs. (in vivo) | % diss. (in vitro) | % abs. (in vivo) | % diss. (in vitro) | % abs. (in vivo) |
| 0 | 0 | 0.0 | 0 | 0.0 | 0 | 0.0 |
| 1 | 15 | 10.6 | 11 | 3.3 | 2 | 0.0 |
| 2 | 24 | 21.1 | 20 | 13.2 | 7 | 0.5 |
| 4 | 36 | 43.2 | 34 | 30.0 | 20 | 15.0 |
| 6 | 47 | 52.3 | 46 | 39.4 | 31 | 23.9 |
| 8 | 55 | 57.8 | 55 | 45.6 | 41 | 29.6 |
| 12 | 69 | 68.6 | 70 | 57.1 | 56 | 41.6 |
| 16 | 79 | 75.5 | 80 | 67.4 | 69 | 51.1 |
| 24 | 90 | 83.6 | 92 | 83.2 | 85 | 64.8 |

In vitro/in vivo correlation plots derived from the data of Table 7 are shown in FIGS. 3-5 for the XR tablets of Examples 1, 2 and 5 respectively.

Estimated PK parameters calculated from predicted steady-state concentrations are given in Table 11.

TABLE 11

Estimated steady-state PK parameters (mean ± standard deviation)

| Parameter | IR tablet (Mirapex ®) | XR tablets | | |
|---|---|---|---|---|
| | | Example 5 | Example 6 | Example 9 |
| $T_{max}$ (h) | | 5.4 ± 1.9 | 5.6 ± 1.3 | 8.0 ± 2.8 |
| $C_{max}$ (ng/ml) | 0.53 ± 0.13 | 0.49 ± 0.15 | 0.48 ± 0.14 | 0.41 ± 0.14 |
| $C_{min}$ (ng/ml) | 0.29 ± 0.14 | 0.22 ± 0.12 | 0.27 ± 0.11 | 0.25 ± 0.15 |
| $C_{avg}$ (ng/ml) | 0.40 ± 0.13 | 0.36 ± 0.14 | 0.38 ± 0.12 | 0.34 ± 0.15 |
| $AUC_{0-\tau}$ (ng · h/ml) | 9.63 ± 3.12 | 8.66 ± 3.29 | 9.00 ± 2.92 | 8.06 ± 3.52 |
| FR | 0.66 ± 0.22 | 0.87 ± 0.31 | 0.61 ± 0.18 | 0.62 ± 0.45 |

The subjects dropped from the study experienced a non-serious adverse event, orthostatic hypotension. Both subjects were receiving treatment with the XR tablet of Example 1 when this adverse event occurred.

No serious adverse events were reported in the study. The most frequently reported event was orthostatic hypotension, all but two of which were considered transient in nature. The numbers of individual non-serious adverse events reported for each treatment are given in Table 12.

TABLE 12

Numbers of non-serious adverse events reported

| | IR tablet | XR tablets | | |
|---|---|---|---|---|
| | (Mirapex ®) | Example 5 | Example 6 | Example 9 |
| No. of subjects | 10 | 12 | 11 | 10 |
| All events | 9 | 17 | 8 | 5 |
| Orthostatic hypotension | 1 | 5 | 2 | 1 |

Discussion

The mean plasma pramipexole concentration profile shown in FIG. 5 clearly shows the tablets of Examples 5, 6 and 9 effectively extended the release of pramipexole relative to the IR tablet. The XR tablets of Examples 5 and 6 exhibit a delay of approximately 1 hour in onset of absorption, whereas quantifiable levels of pramipexole were not observed until about 3 hours after administration of the XR tablet of Example 9.

The derived PK parameters given in Table 9, in particular the $C_{max}$ and $T_{max}$ data, indicate that of the XR tablets, the tablet of Example 5 exhibited the fastest and the tablet of Example 9 the slowest absorption, the tablet of Example 6 being intermediate in this regard.

Figure 6:
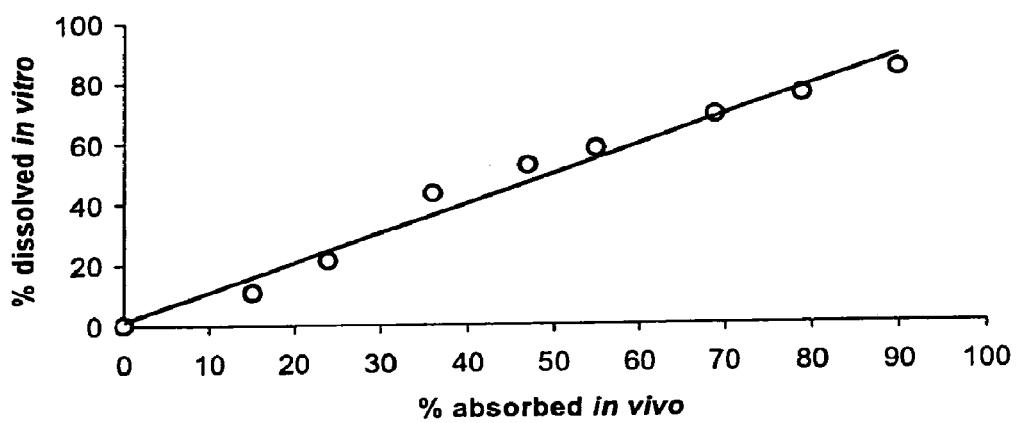
FIG. 6 shows in vitro/in vivo correlation for the 0.375 mg pramipexole dihydrochloride tablets of Example 5.
Figure 7:
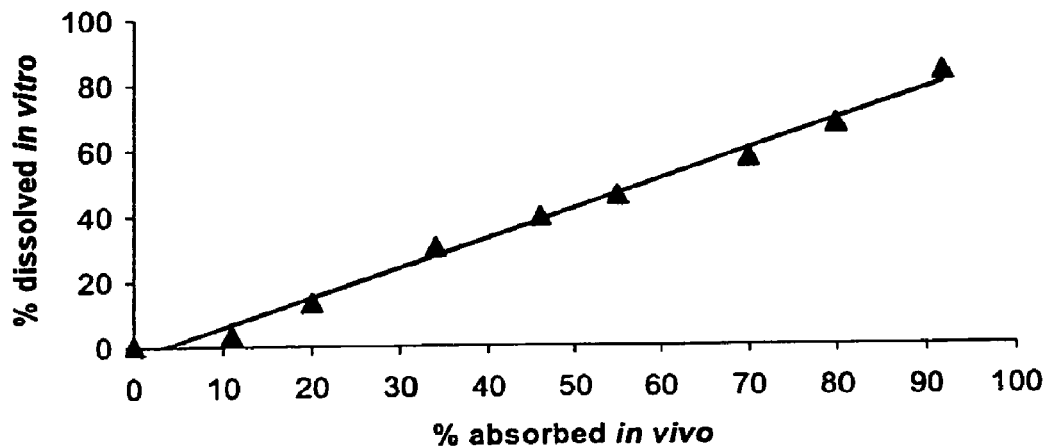
FIG. 7 shows in vitro/in vivo correlation for the 0.375 mg pramipexole dihydrochloride tablets of Example 6.
Figure 8:
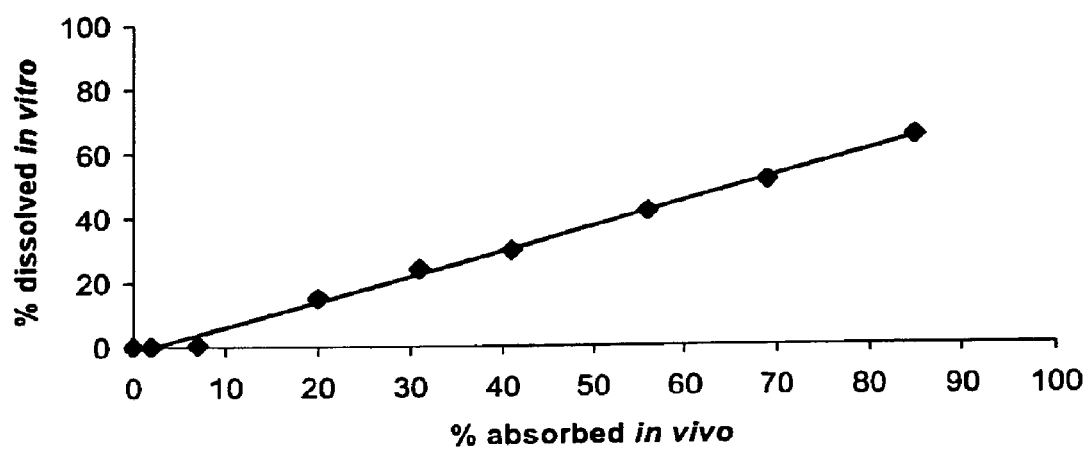
FIG. 8 shows in vitro/in vivo correlation for the 0.375 mg pramipexole dihydrochloride tablets of Example 9.

The relatively high incidence of non-serious adverse events associated with the tablet of Example 5 suggests that the relatively rapid release of pramipexole from this formulation, leading to a relatively high $C_{max}$, is detrimental to the safety profile of such a formulation. On the other hand, the tablets of Examples 6 and 9 exhibit a safety profile that is at least as favorable as the IR tablet administered three times daily. As shown in Table 11, the predicted fluctuation ratio was also greatest for the tablet of Example 5. As shown in FIGS. 6-8, a strong in vitro/in vivo correlation was established within each formulation. Surprisingly, however, the in vitro dissolution data did not clearly distinguish the uncoated tablet of Example 5 from the coated tablet of Example 6, except, as pointed out above, at the earliest sampling times.

What is claimed is:

1. A pharmaceutical composition in a form of an orally deliverable, sustained-release tablet having a core comprising pramipexole dihydrochloride monohydrate in an amount of about 0.375, 0.75, 1.5, 3 or 4.5 mg, dispersed in a matrix comprising (a) hydroxypropylmethylcellulose in an amount of about 35% to about 50% by weight of the tablet and (b) a pregelatinized starch having a tensile strength of at least about 0.15 kN cm$^{-2}$ at a solid fraction of 0.8 as measured using a compact consisting only of said starch, in an amount of about 45% to about 65% by weight of the tablet; said core being substantially enclosed in a coating that constitutes about 2% to about 7% of the weight of the tablet, said coating comprising an ethylcellulose-based hydrophobic or water-insoluble component and an HPMC-based pore-forming component in an amount of about 10% to about 40% by weight of the ethylcellulose-based component, further wherein said tablet provides sustained release as compared with an immediate release pramipexole formulation.

2. The composition of claim 1 wherein the starch has a tensile strength of at least about 0.175 kN cm$^{-2}$.

3. The composition of claim 1 wherein the starch has a tensile strength of at least about 0.2 kN cm$^{-2}$.

4. A method of treatment of a subject having a condition or disorder for which a dopamine D2 receptor agonist is indicated, the method comprising orally administering not more than once daily to the subject the pharmaceutical composition of claim 1.

5. The method of claim 4 wherein the condition or disorder is Parkinson's disease or a complication associated therewith.

6. The composition of claim 1, wherein said composition, when administered once daily, exhibits a bioavailability substantially equivalent to an equal daily dose of an immediate-release pramipexole dihydrochloride reference formulation administered three times a day.

\* \* \* \* \*

UNITED STATES PATENT AND TRADEMARK OFFICE
CERTIFICATE OF CORRECTION

| | |
|---|---|
| PATENT NO. | : 8,399,016 B2 |
| APPLICATION NO. | : 12/716755 |
| DATED | : March 19, 2013 |
| INVENTOR(S) | : Amidon et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 124 days.

Signed and Sealed this
Thirteenth Day of August, 2013

Teresa Stanek Rea
*Acting Director of the United States Patent and Trademark Office*